US005257984A

United States Patent [19]

Kelley

[11] Patent Number: 5,257,984

[45] Date of Patent: Nov. 2, 1993

[54] BLOOD COLLECTOR

[75] Inventor: Thomas F. Kelley, Canton, Mass.

[73] Assignee: Norfolk Scientific, Inc., Norwood, Mass.

[21] Appl. No.: 771,054

[22] Filed: Oct. 2, 1991

[51] Int. Cl.[5] .............. A61B 5/14

[52] U.S. Cl. .............. 604/403; 128/763; 128/764

[58] Field of Search .............. 604/403, 411, 415, 416; 128/763, 764, 770, 771

[56] References Cited

U.S. PATENT DOCUMENTS

| | | | |
|---|---|---|---|
| 2,176,923 | 10/1939 | Nitardy | 604/416 X |
| 2,442,983 | 6/1948 | Nessett | 604/415 X |
| 2,780,225 | 2/1957 | Barr et al. | 604/403 X |
| 3,081,029 | 3/1963 | Gauslaa | 604/415 X |
| 3,141,336 | 7/1964 | Oates | 73/425.4 |
| 3,853,127 | 12/1974 | Spademan | 604/415 X |
| 3,902,477 | 9/1975 | Gerarde | 604/403 X |
| 3,926,521 | 12/1975 | Ginzel | 356/39 |
| 4,024,857 | 5/1977 | Blecher et al. | 128/2 F |
| 4,132,225 | 1/1979 | Whattam | 128/763 |
| 4,314,570 | 2/1982 | Sarstedt | 128/763 |
| 4,393,882 | 7/1983 | White | 128/763 X |
| 4,420,517 | 12/1983 | Ali | 604/403 X |
| 4,758,409 | 7/1988 | Uffenheimer | 422/102 |
| 4,856,533 | 8/1989 | Anraku et al. | 128/763 |
| 5,038,794 | 8/1991 | Van Valkenburg | 604/403 X |

OTHER PUBLICATIONS

*RAM Scientific Specifications*, Capillary Blood Collection Device, product specification sheet, one page with drawings showing "The KABE Collector," undated, from RAM Scientific, P.O. Box 2157, Princeton, NJ.

FIG. 6, "Examples of Plastic Microcollection Devices," p. H14-A, one page with drawings, Cpoyright (undated), ASTM, 1916 Race St., Philadelphia, Pa. 19103, reprinted from *ASTM Standard* E787-81.

FIG. 5, "Natelson Pipet," p. H14-A, one page with drawing, Copyright (undated), ASTM, 1916 Race Street, Philadelphia, Pa. 19103, reprinted from *ASTM Standard* E787-81.

FIG. 4, "Caraway Pipet," p. H14-A, one page with drawing, Copyright (undated), ASTM, 1916 Race Street, Philadelphia, Pa. 19103, reprinted from *ASTM Standard* E787-81.

*Primary Examiner*—Robert A. Hafer
*Assistant Examiner*—Sam Rimell
*Attorney, Agent, or Firm*—Weingarten, Schurgin, Gagnebin & Hayes

[57] ABSTRACT

Apparatus for transferring a blood specimen from a droplet source to a collection tube via a capillary tube. A glass anticoagulant-coated or an untreated capillary tube and a collection tube with a stopper having an X-slit membrane for admission of the capillary tube into the collection tube with the stopper on. A separating gel may be located in the collection tube to provide plasma and serum separation when the collection tube is centrifuged.

3 Claims, 2 Drawing Sheets

BLOOD COLLECTOR

FIELD OF THE INVENTION

This invention relates to blood collectors and more particularly relates to a new and improved blood collector.

BACKGROUND OF THE INVENTION

The collection of blood samples from a patient are integral in the diagnosis of disease, and the monitoring of therapy. One method of collecting blood is commonly referred to as the "fingerstick". This method involves cutting the skin with a lancing device and collecting the blood from the resulting wound.

The earliest collecting devices were glass tubes, sometimes manufactured with special shapes such as tapered ends. About 10 years ago, manufacturers began introducing specially designed plastic collectors in which the collected blood sample could be directly centrifuged to yield serum or plasma. However, these devices have a number of deficiencies.

One problem associated with these prior blood collectors is that most of them rely on gravity which requires that the drop of blood accumulating at the wound must become large enough to flow down a spout or a funnel which is plastic. Plastic is hydrophobic and therefore, non-wetable, which makes the flow of blood down a plastic spout or funnel very difficult. Furthermore, due to the difficult passage of the blood over a plastic surface, the blood may have time to clot before reaching the anticoagulant usually located in or near the bottom of the blood collector. The clotting may be serious enough to block the flow of blood, or microclots may form which interfere with the subsequent analysis of the blood especially the counting of cells in a blood cell counter. Therefore, the prior blood collectors are very technique dependent to prevent the clotting of blood during the blood collection process.

Another problem associated with prior blood collecting devices is that they are generally unsuitable for use with new, smaller, automated blood analyzers developed in recent years. For example, the pipettor associated with one of these newer instruments cannot reach the prepared plasma or serum in most of the prior art collectors because the blood collector is too long and/or too narrow.

Another type called the KABE Collector has several deficiencies which are identified in the detailed description relating to prior art, infra.

SUMMARY OF THE INVENTION

Apparatus for transferring a blood specimen from a droplet source to a collection tube via a capillary tube has a glass anticoagulant-coated capillary tube or a plain untreated tube and a collection tube with a stopper having an X-slit membrane for admission of the capillary tube into the collection tube with the stopper on. A separating gel may be located in the collection tube to provide plasma or serum separation when the collection tube is centrifuged.

The capillary and collection tubes are preferably sold together but separated from each other. This packaging method is more efficient in the use of space. They are assembled by pushing the capillary tube through the slit membrane of the stopper when in place on the collection tube. A colored band preferably identifies the depth of insertion for proper collection without touching any gel that is provided. As is well known in the art the same colored band can also serve to identify the type of anticoagulant contained therein. The blood is allowed to fill the capillary tube by capillary action and to then flow out of the other end of the capillary tube into the collection tube. The capillary tube is then withdrawn and the slit membrane closes, sealing the contents of the collection tube for later centrifuging, if required.

DESCRIPTION OF THE DRAWINGS

Other features and benefits of the invention can be more clearly understood with reference to the specification and the accompanying drawings in which.

DESCRIPTION OF THE PREFERRED EMBODIMENT

Figure 1:
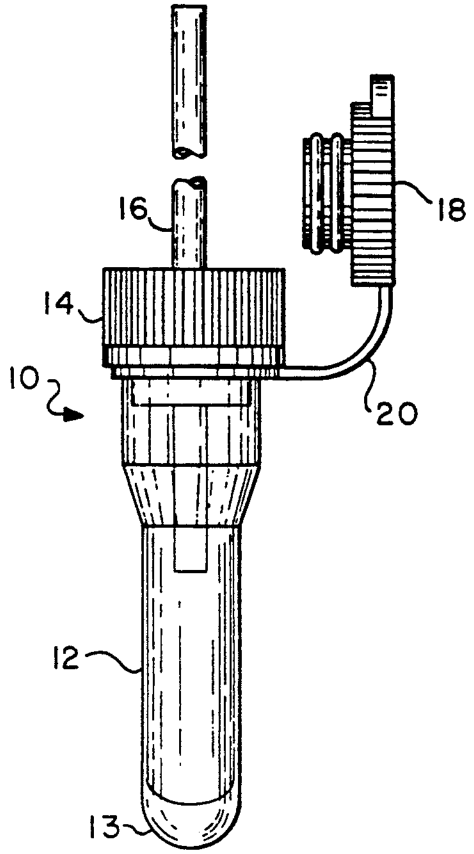
Fig. 1 PRIOR ART
FIG. 1 is a side plan view of a blood collector representatively configured and operable in accordance with the principles of the prior art.

Referring initially to FIG. 1 of the drawing, a blood collection device representatively configured and operable in accordance with the principles of the prior art is indicated generally at 10, and comprises a cylindrical tube 12, into which a pierced stopper 14 rigidly holding a plastic capillary tube 16 is inserted with or without an anticoagulant inner coating. The volume of the tube 12 is large compared to the volume of the plastic capillary tube 16 with the result that the blood sample or the resulting plasma or serum is located near the bottom of the tube making it less accessible to pipetting or pipettors. The unit is sold in this configuration necessitating a plastic capillary to avoid breakage and presenting the risk of the tube being pushed into the gel in transit and/or prior to use and ruining it. The tube 12 having a rounded bottom 13 is unable to stand alone, and requires a support stand or tube rack.

Following specimen collection, the stopper 14 and capillary tube 16 are removed as a unit from the tube 12. The tube 12 is then sealed by inserting an attached plug top 18 into the tube. The plug top 18 is attached to the tube 12 with a tether 20.

Figure 2:
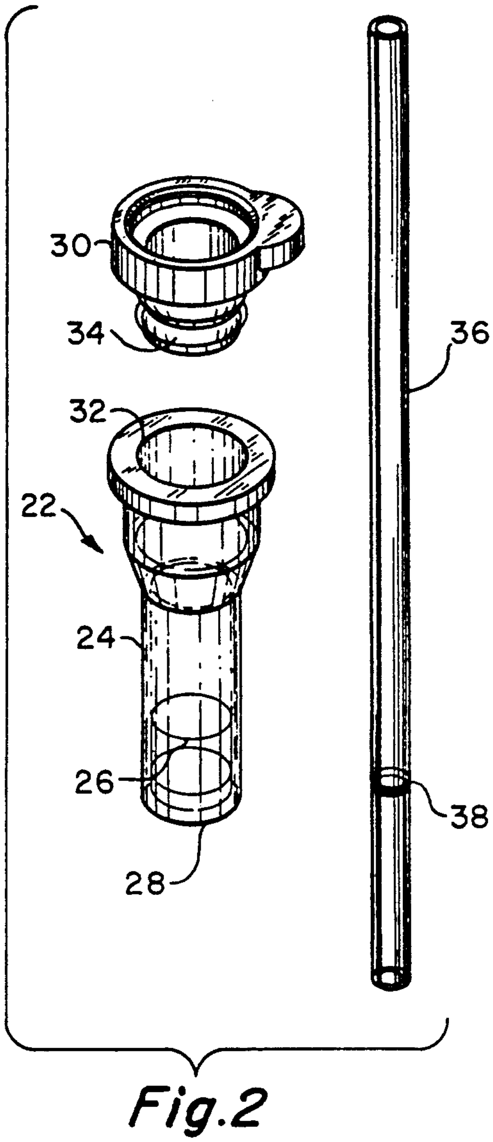
FIG. 2 is a perspective view of a new and improved blood collector.

Referring now to FIG. 2, the new and improved blood collection device is shown generally at 22, and comprises a short cylindrical tube 24 whose volume more closely approximates that of the capillary tube 36, into which a predetermined amount of separation gel 26 has (optionally) been deposited. The tube has a flat or support bottom 28 enabling it to stand unsupported on a flat surface. The tube 24 is sold packaged with a stopper 30 inserted into the mouth 32 of the tube 24.

A glass capillary tube 36 having an insertion alignment ring 38 is also packaged with the unit for sale but provided separately and apart from the stopper 30 allowing a more effective (e.g. hydrophyllic) glass capillary tube to be used. The capillary tube 36 typically has an anti-coagulant coating on its inner surface using the known heparin or EDTA anti-coagulants as examples. The body of the collection tube 24 is typically formed of a plastic or other material suitable for use in and dimensioned for mounting to conventional centrifuging equipment.

Figure 5:
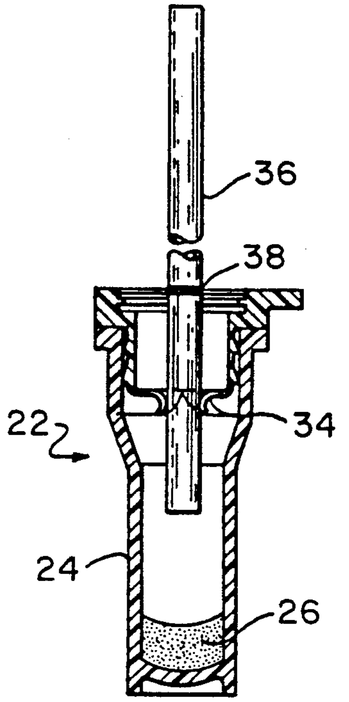
FIG. 5 is a cross-sectional view of the blood collector of FIG. 2 with the capillary tube in position.
Figure 3:
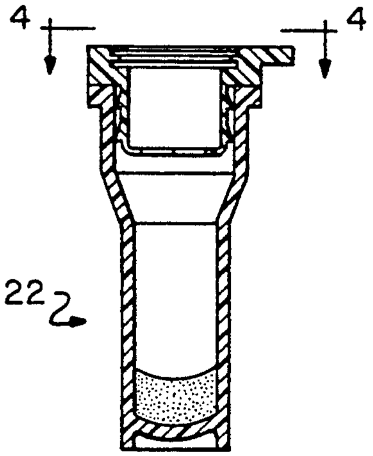
FIG. 3 is a cross-sectional view of the blood collector of FIG. 2.
Figure 4:
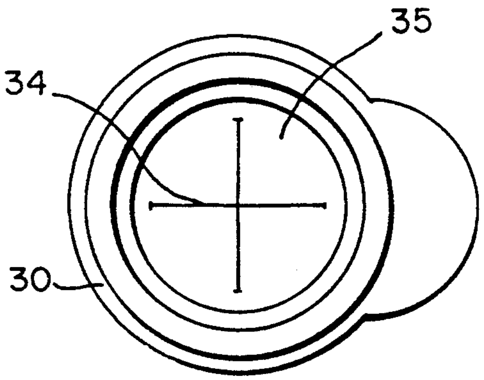
FIG. 4 is a top plan view of the blood collector of FIG. 3.

In use, and as illustrated in FIGS. 3, 4 and 5, the tube 24 I has the stopper 30 fitted in it at the point of sale providing a closure formed by an X shaped slit 34 in a membrane 35 closing the mouth of the tube. The operator inserts the capillary 36 to the point where the mark 38 is aligned with the top of the stopper 30. This insures proper positioning of the capillary tube 36 and avoids the danger of the capillary tube 36 being pushed into a gel 26 which is typically provided at the bottom of the tube 24 for plasma and serum separation.

Figure 6:
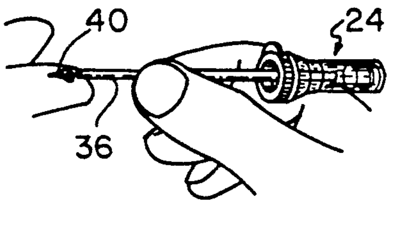
FIG. 6 shows the blood collector being used to obtain a specimen.
Figure 7:
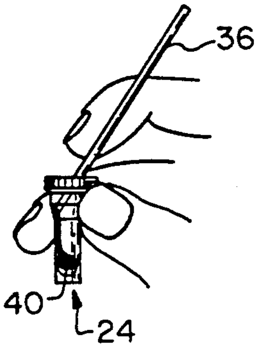
FIG. 7 shows the specimen being drained into the collection device.

The operator then pierces an appropriate skin region as illustrated in FIG. 6 to allow a first droplet 40 of a blood to accumulate. With the capillary tube 36, still inserted in the collection tube 24, in a roughly horizontal or slightly inclined position the mouth of the tube 36 is touched to the droplet 40 causing, by capillary action, the tube 36 to fill with the blood from the droplet 40. At this point the capillary tube 36 and collection tube 24 are turned vertical allowing the blood to flow into the bottom of the collection tube 24. Any remaining portion of blood in the tube 36 may typically be wicked off by touching the inner end of the capillary tube 36 to the inner wall of the collection tube 24. Additional emptying of the capillary tube 36 may be accomplished by use of a small pipette bulb, as is known in the art, applied to the outer end of the capillary tube 36.

If the capillary tube 36 of the apparatus 22 contains an anticoagulant, the collecting tube 24 can be centrifuged immediately to yield plasma. In addition, the blood in the collecting tube 24 is immediately available for analyses on whole blood such as the counting of the blood cells.

If the capillary tube contains no anticoagulant, the thus filled collection tube 24 is then typically allowed to stand for half an hour and allowed to clot before centrifuging to yield serum.

Where it is desired to collect more anticoagulated blood than can be delivered by a single capillary tube 36 it is preferable to use separate tubes because the dosage of anti-coagulant applied to each capillary tube 36 is usually only sufficient to provide anti-coagulant protection to that amount of blood. Typically after the droplets 40 have been transferred to the bottom of the collection tube 24 it will be briefly shaken in order to insure complete mixing of blood and anti-coagulant.

If the capillary tube 36 contains n anticoagulant then the inner end of the capillary tube can be put in contact with the inner wall of the collection tube 24 and a continuous flow of blood established filling the collection tube to its capacity.

The above described embodiments of the present invention are presented by way of example only. The scope of the invention being limited solely as indicated in the following claims.

I claim:

1. A method for the collection of blood comprising:

providing:

a collection tube having a mouth portion and a base portion wherein said base portion is flat, thereby permitting stable vertical orientation of the collection tube without external support means;

a single stopper adapted to seal to said mouth of said collection tube and providing a separate mouth to said collection tube with a penetrating seal therein;

a glass capillary tube, having a reference mark thereon, adapted to be pushed through at least one slit in a membrane of said penetrating seal to a predetermined depth of insertion for conducting blood from an exterior end of said glass capillary tube to the interior of said collection tube; and a merchandising package having at least first and second sealed compartments, said first compartment protectively containing said collection tube with said single stopper installed therein, and said second compartment protectively containing said glass capillary tube;

removing from said merchandising package:

said glass capillary tube, and said collection tube;

inserting said first end of said glass capillary tube through said at least one slit and into said collection tube to align said alignment ring with said membrane of said stopper and form an assembled collection system;

piercing an appropriate skin region on a patient and allowing a quantity of said patient's blood to form proximate to said appropriate skin region;

orienting said assembled collection system so that said glass capillary tube and said collection tube are substantially horizontal;

placing said second end of said glass capillary tube into contact with said quantity of blood;

allowing a blood sample from said quantity of said patient's blood to fill said glass capillary tube;

orienting said assembled collection system vertically, allowing said blood sample to flow from said glass capillary tube into said collection tube forming a collected sample;

draining a remaining amount of said blood sample from said glass capillary tube into said collection tube by placing said first end of said glass capillary tube against said interior surface of said collection tube at a point above said collected sample; and removing said glass capillary tube from said collection tube.

2. The method of claim 1, wherein said glass capillary tube inner surface includes an anticoagulant.

3. The method of claim 2, wherein further including the step of shaking the collection tube after removal of said capillary tube enabling a homogeneous mixture of anticoagulant in said collected sample.

* * * * *

UNITED STATES PATENT AND TRADEMARK OFFICE

CERTIFICATE OF CORRECTION

PATENT NO. : 5,257,984

DATED : November 2, 1993

INVENTOR(S) : Thomas F. Kelley

It is certified that error appears in the above-indentified patent and that said Letters Patent is hereby corrected as shown below:

Column 3, line 9, "24 I has" should read --24 has--.

Column 3, line 56, "contains n" should read --contains no--

Signed and Sealed this

Twenty-third Day of August, 1994

Attest:

BRUCE LEHMAN

*Attesting Officer* *Commissioner of Patents and Trademarks*